(12) United States Patent
Brain et al.

(10) Patent No.: US 10,336,795 B2
(45) Date of Patent: Jul. 2, 2019

(54) SYSTEM AND METHOD FOR PRODUCING PHYCOCYANIN

(71) Applicant: University of Newcastle upon Tyne, Newcastle upon Tyne (GB)

(72) Inventors: Chelsea Marie Brain, Newcastle upon Tyne (GB); Gary Stephen Caldwell, Ashington (GB)

(73) Assignee: University of Newcastle, Newcastle (GB)

( * ) Notice: Subject to any disclaimer, the term of this patent is extended or adjusted under 35 U.S.C. 154(b) by 0 days.

(21) Appl. No.: 15/889,936

(22) Filed: Feb. 6, 2018

(65) Prior Publication Data
US 2018/0155401 A1 Jun. 7, 2018

Related U.S. Application Data

(62) Division of application No. 15/112,646, filed as application No. PCT/GB2015/050183 on Jan. 27, 2015, now Pat. No. 10,072,052.

(60) Provisional application No. 62/013,479, filed on Jun. 17, 2014, provisional application No. 61/931,723, filed on Jan. 27, 2014.

(51) Int. Cl.
| | |
|---|---|
| C12N 9/22 | (2006.01) |
| C07K 14/415 | (2006.01) |
| C09B 61/00 | (2006.01) |
| C09D 11/037 | (2014.01) |
| C09D 11/32 | (2014.01) |
| A61K 8/49 | (2006.01) |
| A61Q 19/00 | (2006.01) |
| C12M 1/00 | (2006.01) |
| A61K 8/30 | (2006.01) |
| A23L 29/269 | (2016.01) |

(52) U.S. Cl.
CPC .......... *C07K 14/415* (2013.01); *A23L 29/269* (2016.08); *A61K 8/30* (2013.01); *A61K 8/492* (2013.01); *A61Q 19/00* (2013.01); *C09B 61/00* (2013.01); *C09D 11/037* (2013.01); *C09D 11/32* (2013.01); *C12M 21/02* (2013.01); *C12M 31/02* (2013.01); *A61K 2800/10* (2013.01); *A61K 2800/43* (2013.01)

(58) Field of Classification Search
None
See application file for complete search history.

(56) References Cited

U.S. PATENT DOCUMENTS 10,072,052 B2 * 9/2018 Brain .................. C09D 11/037

FOREIGN PATENT DOCUMENTS

JP 2002-315569 10/2002

OTHER PUBLICATIONS

Wang, C.-Y., Fu, C.-C., and Liu, Y.-C., *Effects of using light-emitting diodes on the cultivation of Sqirulina platensis* (2007) Biochem. Engineer. J., 37(1): 21-25
Walter, A., Cesar de Carvalho, J ., Soccol, V.T., Bisinella de Faria, A.B., Ghiggi, V., and Soccol, C.R., *Study of Phycocyanin Production from Sqirulina platensis Under Different Light Spectra* (2011) Brazil. Arch. Biol. Tenchnol. 54(4): 675-682.
Bryant, D.A., *The Photoregulated Expression of Multiple Phycocyanin Species* (1981) Eur. J. Biochem. 119: 425-429.
Takano, H., Arai, T., Hirano, M., and Matsunaga, T. *Effects of intensity and quality of light onhycocyanin production by a marine cyanobacterium Synechocuccus sp. NKBG 042902* (1995) Appl. Microbiol. Biotechnol., 43: 1014-1018
Dai, Y.-J., Li, J., Wei, S.-M., Chen, N., Xiao, Y.-P., Tan, Z.-L., Jia, S.-R., Yuan, N.-N., Tan, N., and Song, Y.-J., *Effect of Light with Different Wavelengths on Nostoc flagellitorme Cells in Liquid Culture* (2013) J. Microbiol. Biotechnol. 23(4): 534-538.
Ahluwalia, A.S., Rai, R.K., and Kumar, H.D., *Chromatic adaptation and photoreversal in blue-green alga Calothrix clavata West* (1980) J. Biosci. 2(1): 63-68.
Lopez-Bautista, J. M., *Red Algal Genomics: A Synopsis In: Red Algae in the Genomic Age, Cellular Origin, Life in Extreme Habitats and Astrobiology*, (2010) 13: 227-240, Seckbach, J. and Chapman, D.J. (eds).
Bryant, D.A., de Lorimier, R., Guglielmi, G., and Stevens, S.E., *Structural and compositional analyses of the phycobilisomes of Synechococcus sp. PCC 7002. Analyses if the wild-type strain and a phycocyanin-less mutant constructed by interposon mutagenesis* (1990) Arch. Microbiol. 153: 550-560
Markou, G., *Effects of various colors of light-emitting diodes (LEDs) on the biomass composition of Arthronira platensis cultivated in semi-continuous mode* (2014) Appl. Biochem. Biotechnol. 172: 2758-2768.

* cited by examiner

*Primary Examiner* — Hope A Robinson
(74) *Attorney, Agent, or Firm* — Matthew Kaser; Adam Warwick Bell

(57) ABSTRACT

The invention discloses microorganism cell culture conditions that result in increased cellular and media concentrations of a biological pigment. The invention has applications in use as a natural food coloring, as antioxidants in the food supplement industries, in the nutraceutical, pharmaceutical, and cosmeceutical industries, and a non-toxic ink. The method results in pigment that is relatively easy to separate from the microorganism culture.

5 Claims, 6 Drawing Sheets

Typical white LED Peak ———
Typical red LED Peak – – –
Red 680 nm LED Peak ··········

SYSTEM AND METHOD FOR PRODUCING PHYCOCYANIN

RELATIONSHIP TO OTHER APPLICATIONS

This application claims priority to and benefits of the following: U.S. Provisional Patent Application No. U.S. 61/931,723 filed 27 Jan. 2014, entitled "Improvements in the Synthesis of Phycocyanin", U.S. Provisional Patent Application No. U.S. 62/013,479 filed 17 Jun. 2014, entitled "Synthesis of Phycocyanins", International Patent Application number PCT/GB2015/050183, filed 27 Jan. 2015, entitled "Improvements in the Synthesis of Phycocyanins", and United States National Phase Non-provisional patent application Ser. No. 15/112,646 filed 19 Jul. 2016 under 35 U.S.C. § 371, entitled "Improvements in the Synthesis of Phycocyanins", now allowed and issued on 11 Sep. 2018 as U.S. Pat. No. 10,072,052, which are all herein incorporated by reference in their entirety for all purposes.

FIELD OF THE INVENTION

The present invention relates to using microbial cell culture conditions that result in increased levels and concentrations of pigments.

BACKGROUND

Phycocyanin (PC) is a blue pigmented billiprotein, a chromophore produced in prokaryotic cyanobacteria as well as certain eukaryotes such as the rhodophytes, cryptomonads and glaucocystophytes. PC is increasingly being exploited as a natural food colouring, replacing the synthetic dye Brilliant Blue FCF that has been associated with health problems; PC is particularly suited to this use because of its high solubility in water and stability over a large pH range [1]. In addition, PC is used in the nutraceutical, pharmaceutical and cosmeceutical industries at higher purities for its anti-oxidant and anti-inflammatory properties, together with other associated health benefits [2-4]. PC in its more crude form is also used as an additive to animal feeds to enhance the colour of ornamental fish and birds. At its highest quality and purity PC is used in laboratory assay kits for its fluorescent properties. There is also early but ongoing research into the therapeutic properties of PC for medical use [5]. The PC market is in its infancy.

In cyanobacteria, PC is present in the thylakoid membranecomplexed with the other biliproteins including phycoerythrin (PE) and allophycocyanin (AP or APC) which together function as a light-harvesting apparatus known as the phycobillisome [6]. The phycobillisome absorbs specific wavelengths of light that cannot be utilized by chlorophyll, thereby increasing the efficiency of photosynthesis [7]. PC absorbs maximally at 610-620 nm with PE (540-570 nm) and APC (650-655 nm) [6].

Cyanobacteria are widely used in aquaculture for PC production with the eukaryotes showing potential for future exploitation. Among the cyanobacteria the genus *Arthrospira* (formerly known as *Spirulina* and still commercially known as '*Spirulina*') is the most commonly cultured genus; however, PC has been extracted from other genera such as *Aphanizomenon* and *Anabaena*. The main species in culture are *Arthrospira platensis* and *A. maxima*. These are both filamentous cyanobacteria with spiral-shaped filaments or trichomes.

In addition to its high PC content, spirulina also contains high amounts of other nutraceuticals such as vitamins and PUFAs and is high in single cell protein; as a result, PC is becoming of increasing commercial interest in the West [1]. In the East and Africa however, *Spirulina* has been used as a food for many centuries [9]. *Spirulina* biomass is a salable product alone, however pure phycocyanin, depending on purity has a considerably higher market price.

As water molecules absorb in the far red region of light, limitations in this wavelength for photosynthesis occur in the natural algae environment [6]. Light scattering of shorter wavelengths also occurs by suspended material resulting in the provision bias of blue-green wavelength light to algae in nature. Therefore environmental factors determine light availability and algae can adapt to utilize quality and quantity of light available.

Some cyanobacteria containing PE and PC exhibit a phenomenon called complementary chromatic adaptation where PC:PE ratio is altered in response to different light regimes by modulating synthesis [10,11]. Recent research has shown that *A. platensis* can be manipulated in the presence of certain wavelengths of light to increase production of PC.

By using light filters Walter et al. (2011) [12] demonstrated increased PC purity under red light (600-700 nm). Earlier research by Wang et al. also found *A. platensis* biomass productivity was higher culturing under red light [13]. The calculations by Wang et al. demonstrated that the use of red light would be economically beneficial to photoautotrophic production, as energy to biomass conversion is more efficient. Farges, 2009 [19] also modeled growth of *A. platensis* under polychromatic and monochromatic light sources, demonstrating mathematical increases in culturing efficiency under red 620 nm LEDs through decreased electrical energy power consumption with maintained and comparable growth rates; however monochromatic red LED light (620 nm) was shown to decrease the PC concentration of *A. platensis* by 2-fold, compared with white/polychromatic and red+blue polychromatic LEDs. These studies have demonstrate that culturing under different wavelengths of light can effect the PC concentration and purity in *A. platensis* cultures, however tests have not been conducted using wavelengths above that of normal red LEDs.

There is therefore a need in the art for improved and less costly methods for synthesis of phycocyanins.

SUMMARY OF THE INVENTION

The invention herein disclosed provides for devices and methods that may be used for the improved synthesis of phycocyanins. The method results in a greater than 10-fold increase in phycocyanin levels, a clear improvement over the prior art. The method also results in an improvement for harvesting phycocyanins.

The devices herein disclosed may be used in many applications, including, but not limited to, use as a natural food colouring, as an antioxidant in the food supplement industries, in the nutraceutical, pharmaceutical, and cosmeceutical industries, and as a non-toxic ink.

The invention provides improved methods for the synthesis and commercial production of phycocyanins and other natural biochemical compositions, including but not limited to, hyaluronans, glucosamines, other saccharides and/or polysaccharides, other phycobiliproteins, such as but not limited to, allophycocyanin, phycoerythrin, bilin, phycobilin, proteoglycans, glycosaminoglycans, and the like.

In one embodiment, the method includes providing a microorganism capable of synthesizing phycocyanins, providing a suitable culture and growth medium, illuminating the microorganism in culture with red and/or near-infrared light, and in the alternative, illuminating the microorganism in culture with red and/or near-infrared monochromatic light. In an alternative embodiment, the method also provides illuminating the microorganism in culture with white light.

In another embodiment, the method includes providing an organism capable of photosynthesizing carbon-based compositions using energy from a natural or an artificial energy source. The organism may be a photosynthetic bacterium, photosynthetic archaean, a photosynthetic protist, a photosynthetic alga, a photosynthetic moss, or a photosynthetic plant. The organism may be a naturally occurring species or it may be a synthetic organism created using recombinant DNA technology. The organism may be a domesticated plant species and may also comprise DNA from another organism.

In one embodiment the near-infrared light comprises electromagnetic radiation having a wavelength between about 630 nm and about 720 nm. In another embodiment the near-infrared monochromatic light comprises electromagnetic radiation having a wavelength of about 680 nm. In an alternative embodiment the near-infrared monochromatic light comprises electromagnetic radiation having a wavelength of about 678 nm. In another alternative embodiment the near-infrared monochromatic light comprises electromagnetic radiation having a wavelength of about 682 nm. In one embodiment the white light comprise electromagnetic radiation having wavelengths between about 350 nm and about 760 nm. In another alternative embodiment the near-infrared monochromatic light comprises electromagnetic radiation having a wavelength of about 650 nm. In yet another alternative embodiment the near-infrared monochromatic light comprises electromagnetic radiation having a wavelength of about 720 nm. In yet another alternative embodiment the monochromatic light comprises electromagnetic radiation having a wavelength of between about 450 and 590 nm.

In another embodiment the red light consists of electromagnetic radiation having wavelengths between 640 nm and 720 nm. In another embodiment the red light consists of electromagnetic radiation having wavelengths between 640 nm and 1000 nm. In another embodiment the red light consists of electromagnetic radiation having a maximum wavelength emission of 680 nm. In an alternative embodiment the red light consists of electromagnetic radiation having a wavelength of 678 nm. In another alternative embodiment the red light consists of electromagnetic radiation having a wavelength of 682 nm. In one embodiment the white light consists of electromagnetic radiation having wavelengths between 350 nm and 760 nm.

In another preferred embodiment, the synthesized phycocyanin leaches from the microorganism.

In another embodiment, the microorganism capable of synthesizing phycocyanins is cultured in a pond system or open raceway system. In a preferred embodiment, >640 nm LED rods are placed in the pond system or open raceway system and which results in increased synthesis of phycocyanins in the microorganism.

In another embodiment the invention contemplates a system for producing phycocyanins, the system comprising a vessel and a lamp, wherein the lamp generates electromagnetic energy having a wavelength of at least 640 nm or greater, and wherein the vessel further comprises a microorganism capable of synthesizing phycocyanin.

GENERAL DISCLOSURES

Figure 1:
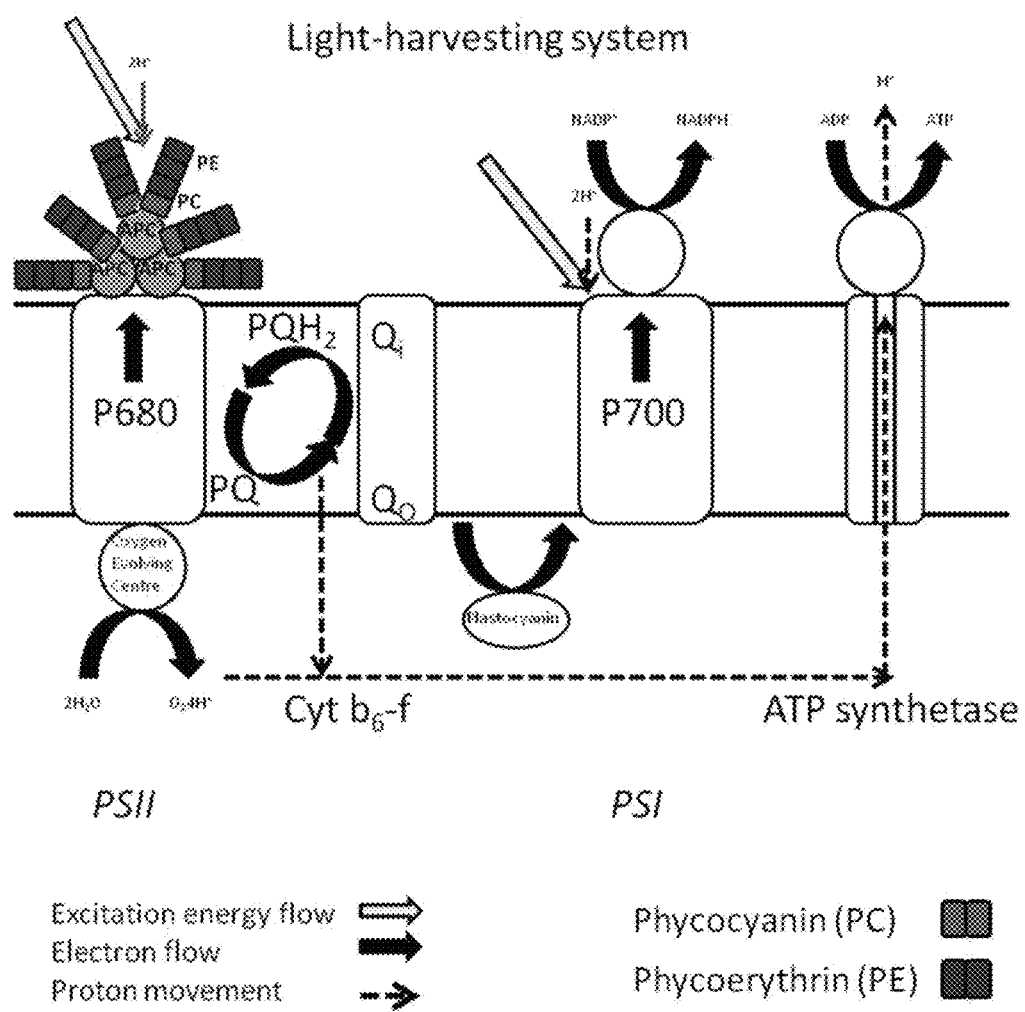
FIG. 1. Schematic of the energy conversion process in photosynthesis. P680 and P700 represent the reaction centre Chl a of Photosystem II and Photosystem I respectively. Phycocyanin (PC) (610-620 nm) is present in a complex with Phycoerythrin (PE) (540-570 nm) and Allophycocyanin (APC) for the phycobilisome light harvesting apparatus which absorb specific wavelengths of light for use in photosynthesis.

The embodiments disclosed in this document are illustrative and exemplary and are not meant to limit the invention.

Other embodiments can be utilized and structural changes can be made without departing from the scope of the claims of the present invention.

As used herein and in the appended claims, the singular forms "a," "an," and "the" include plural reference unless the context clearly dictates otherwise. Thus, for example, a reference to "a particle" includes a plurality of such particles, and a reference to "a surface" is a reference to one or more surfaces and equivalents thereof, and so forth.

The symbol "≥" when used in the context of the wavelength of electromagnetic radiation, means "greater than or equal to"; the term "≥640 nm" means electromagnetic radiation having a wavelength of at least or greater than 640 nm, for example, 640 or 641 nm.

The term "about" when used in the context of electromagnetic radiation wavelength means a wavelength of within 2 nm of the wavelength as written; therefore the term "a wavelength of about 640 nm" means the electromagnetic wavelength is between 638 nm and 642 nm.

DETAILED DESCRIPTION OF THE INVENTION

The invention herein disclosed provides for devices and methods that may be used for the synthesis of phycocyanins. The method results in a greater than 4.5-fold $_{[CMB1]}$ in phycocyanin levels, a clear improvement over the prior art $_{[CMB2]}$. The devices herein disclosed may be used in many applications, including, but not limited to, use as a natural food colouring, as an antioxidant in the food supplement industries, in the nutraceutical, pharmaceutical, and cosmeceutical industries, and as a non-toxic ink. The invention provides improved methods for the synthesis and commercial production of phycocyanins.

In an exemplary embodiment, the method includes providing a microorganism capable of synthesizing phycocyanins, providing a suitable culture and growth medium, illuminating the microorganism in culture with red and/or near-infrared light, and in the alternative, illuminating the microorganism in culture with red and/or near-infrared monochromatic light. In an alternative embodiment, the method also provides illuminating the microorganism in culture with white light.

In one embodiment the red light consists of electromagnetic radiation having wavelengths between about 640 nm and about 720 nm. In another embodiment the red light consists of electromagnetic radiation having wavelengths between 640 nm and 1000 nm. In another embodiment the red light consists of electromagnetic radiation having a maximum wavelength emission of 680 nm. In an alternative embodiment the red light consists of electromagnetic radiation having a wavelength of 678 nm. In another alternative embodiment the red light consists of electromagnetic radiation having a wavelength of 682 nm. In another alternative embodiment the red light consists of electromagnetic radiation having a wavelength of 690 nm. In another alternative embodiment the red light consists of electromagnetic radiation having a wavelength of 670 nm. In an alternative embodiment the red light consists of electromagnetic radiation having a mean wavelength of 680 nm, wherein the wavelength is within a 95% confidence interval of 640-720 nm. In one embodiment the white light consists of electromagnetic radiation having wavelengths between 350 nm and 760 nm.

Culturing under red 680 nm LED light compared to white was shown to increase PC production in *A. platensis* by an average of 5-fold and these effects could be seen visually in the cultures. Mass spectral analysis has shown some major differences and changes on the protein level through culturing under the two different light sources. $_{[CMB3]}$ No significant difference was seen in growth rate under the two light sources $_{[CMB4]}$.

The invention will be more readily understood by reference to the following examples, which are included merely for purposes of illustration of certain aspects and embodiments of the present invention and not as limitations.

EXAMPLES

Example I: Batch Cultures

Figure 2:
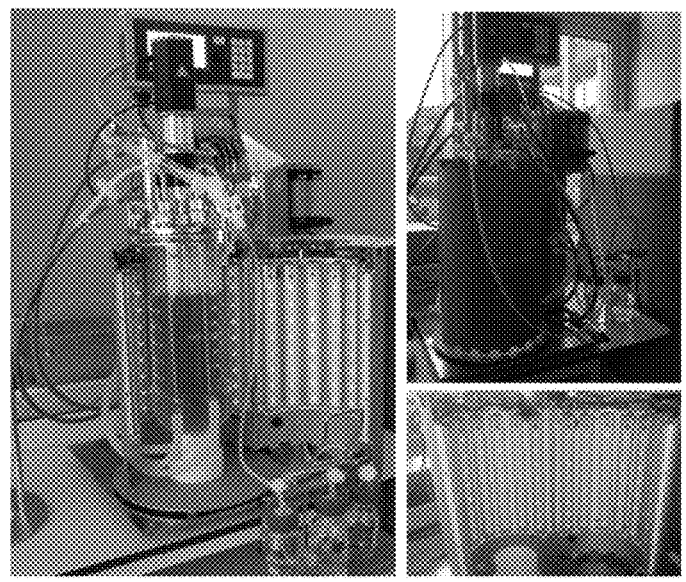
FIG. 2. The Infors stirred-tank photobioreactor shown with red (left) and white (bottom right) LED jackets and closed jacket during normal operation (top right). Technical data: Infors cell culture system impeller (1 pitched blade impeller, 3 blades), flow direction: upwards, Angle: 45 degrees, Dimensions: A diameter, B height, C length across blade: A=65 mm, B=52 mm, C=72 mm Vessel: Total volume 3.6 liters, Inner diameter: 115 mm, Height 370 mm.
Figure 3:
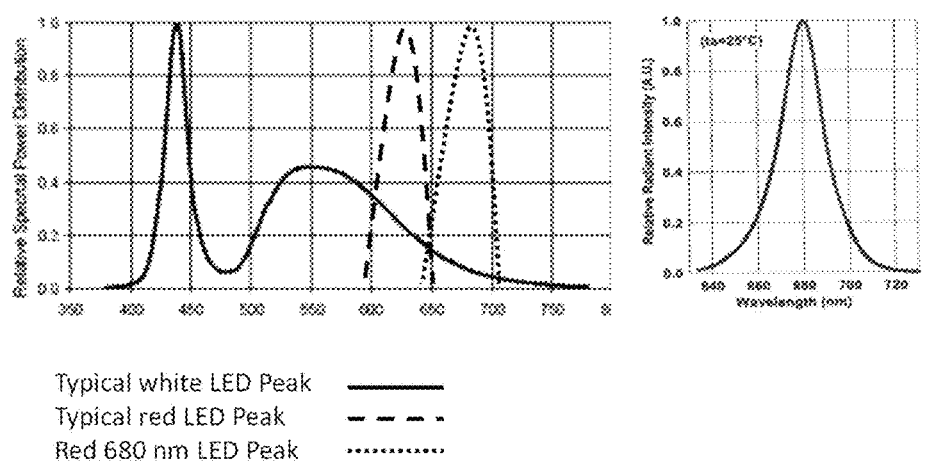
FIG. 3. Typical emission spectra comparing typical white LED, typical red LED (typically around 620-640 nm) and EPITEX 680 nm LED light. Right shows emission spectra of EPITEX 680 nm LED emitting narrow intense light with an optimum emission wavelength of 680 nm.

F/2 sterile medium (CCAP [Culture Collection of Algae and Protozoa] recipe) supplemented with 2.5 g/l NaNO$_3$ (pH 8) was inoculated under aseptic conditions at 20% (v/v) with *Arthrospira platensis* (CCMP [Culture Collection of Marine Phytoplankton] 1295/Bigelow Laboratory US) (OD 0.11-0.12) in logarithmic growth phase. A stirred tank photobioreactor (STPBR) (Infors Labfors 4 benchtop modified bioreactor) with either white (Lumitronix Barre LED High-Power SMD 600 mm, 12 V) or 680 nm Red LEDs (FIGS. 2 and 3) was operated with 2.75 l of culture at 30° C. and 45 µmol$^{-1}$ m$^{-2}$ light intensity with 18:6 light:dark cycle and impeller speed 200 rpm with natural compressed air (~0.03% CO$_2$) supplied at 0.08 LPM (VVM (volume of air per volume of culture per minute) ~0.03 liters air per liters medium per minute, LPM) through a gauzed ring sparger. pH and dissolved oxygen was recorded online in 10 minute periods (Mettler Toledo probes). 8 ml samples were taken aseptically on days 1 (inoculation), 3, 6, 7, 10, 13, and 14 for analysis.

Example II: Growth Measurement

Optical density (OD) was used alongside chlorophyll autofluorescence (CF) and direct cell counts as a proxy for growth. OD was measured in triplicate at 750 nm Griffiths et al. (2011) [14] using a Cary 100 UV/Vis Spectrophotometer (Varian) corrected with F/2 medium. CF was analysed in three triplicate 300 µl samples divided into individual wells of a black 96 well plate. Samples were excited at 430 nm and emission measured at 690 nm using a FLUOstar OPTIMA fluorescence plate reader (BMG LABTECH). Readings were taken against blank samples of F/2 medium and the average values in arbitrary fluorescence units used for statistical analysis. Cell counts were performed using a Sedgewick rafter counting cell and using Leitz Dialux 20 light microscope. Triplicate 10 random sample counts were taken for 1 µl of culture.

Example III: Morphological Assessment

The total length and width of the spirals of 20 cyanobacteria were measured to assess any changes in the morphological features of the trichomes. Images were taken using Leitz Dialux 20 light microscope and EasyGrab software with analysis performed using Image J. Image size was calibrated using graticules at 630 pixels mm$^{-1}$.

Example IV: Phycocyanin Analysis

PC extraction was based on the method by Zhang and Chen (1999) [15]. 5 mL samples were harvested by centrifugation at 3000 g/10 minutes (Sigma 3K18C centrifuge) in pre-weighed glass tubes. Cells were washed once in deionized water and the wet biomass weighed. The pellet was then resuspended in 3 mL 0.05 M sodium phosphate buffer (pH7). Cells were disrupted by a freeze/thaw cycle (−20° C.) over 1 hour and sonicated for 3 minutes at 6 microns amplitude (Soniprep 150, MSE). Samples were then centrifuged at 10,000 g, 30 minutes (Sigma 1-15 microcentrifuge) and the absorbance of the supernatant scanned over 200-800 nm by spectrophotometer (Cary 100 UV-Vis spectrophotometer, Varian) using a quartz cuvette. Sodium phosphate buffer (0.05 M) was used as a blank and the PC concentration and purity calculated using the method by Bennet and Bogorad (1973) [10] (Equation 1) and Boussiba and Richmond (1979) [16] (Equation 2) respectively. Extraction yield was calculated as below in Equation 3. PC concentration was analysed at day 14 (or when growth reached OD 0.33) as three replicates.

1. PC (mg/mL)=(A620−0.474 (A655))/5.34.
2. PC purity=A620/A280.
3. Extraction yield (mg PC/g biomass)=(PC concentration*volume of solvent (mL)/wet biomass (g)

Example V: Mass Spectrometry (MS) Analysis

Matrix Preparation:
20 mg alpha-Cyano-4-hydroxycinnamic acid (HCCA) (Brucker Daltonics) was mixed with 1 ml 50% acentonitrile:2.5% TFA solution and saturated by 30 minutes incubation at 25° C. in an ultrasonic water bath (Grant instruments, Cambridge), vortexed at 15 minutes. Matrix was centrifuged (14,000 g, 1 minutes) (Sigma 1-15K microcentrifuge) and 50 µl aliquots prepared fresh for use.

Sample Preparation:
1 ml samples were centrifuged (14,000 g, 5 minutes) (Sigma 1-15K microcentrifuge) and the pellet washed twice in fresh deionized water (fdw) and stored frozen at −80° C. Pellets were thawed on ice and resuspended in 50 µl fdw before spotting. Samples were mixed 1:1 with HCCA matrix and 4 µl duplicate samples spotted onto a steel target plate (MTP 384 target plate ground steel, Brucker) along with 1 µl bacterial standard (Brucker) layered with 1 µl HCCA matrix as a calibrant. Samples then underwent MS analysis (Bruker ultraflex II MALDI-TOF). Spectra were analysed using flexAnalysis software package (Bruker).

Example VI: Population Analysis

Samples were frozen in 15% sterile Glycerol and frozen at −80° C. for population analysis (Dr Andrew Free and Rocky Kindt, Edinburgh University).

Example VII: Statistical Analysis

Data analysis was performed using Microsoft Excel 2007 and Graphpad Prism 5.

Example VIII: Results: Growth

Figure 4:
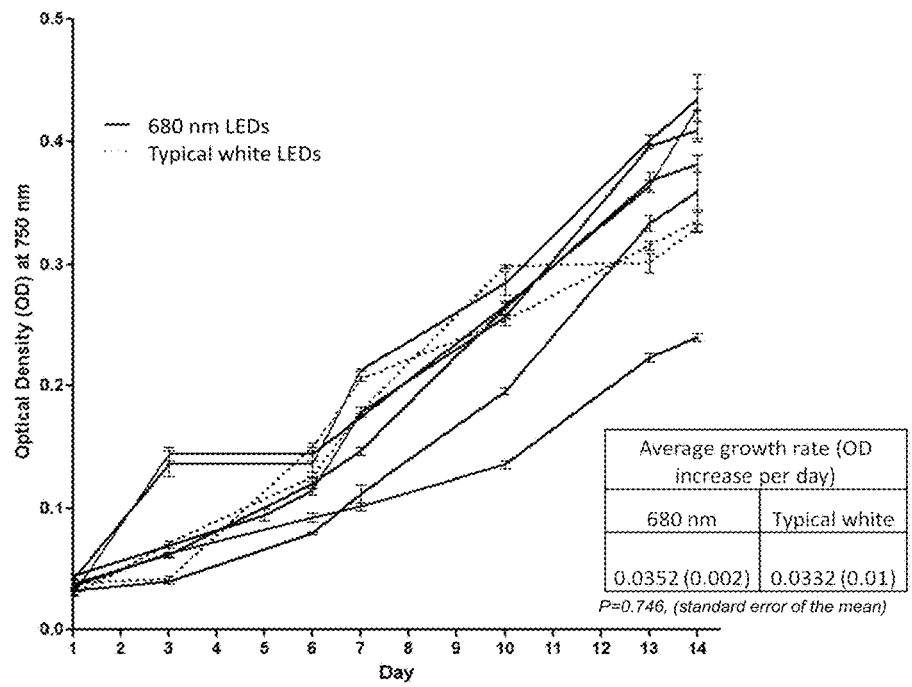
FIG. 4. Growth curves for separate batch runs of *A. platensis* culture (error bars represent standard error of the mean) with table showing average growth rate of *A. platensis* under 680 nm LEDs compared to typical white LEDs, with no significant difference in growth under the two light conditions.

No significant difference in growth of cultures was observed under red 680 nm compared to white LED light (FIG. 4). Note the large acclimatization lag period in batch Red 2 (FIG. 4). The culture required a period to acclimatize to be able to utilize the red 680 nm light in photosynthesis (from observation), and this acclimatization was reversible.

Example IX: Results: PC Analysis

Figure 5:
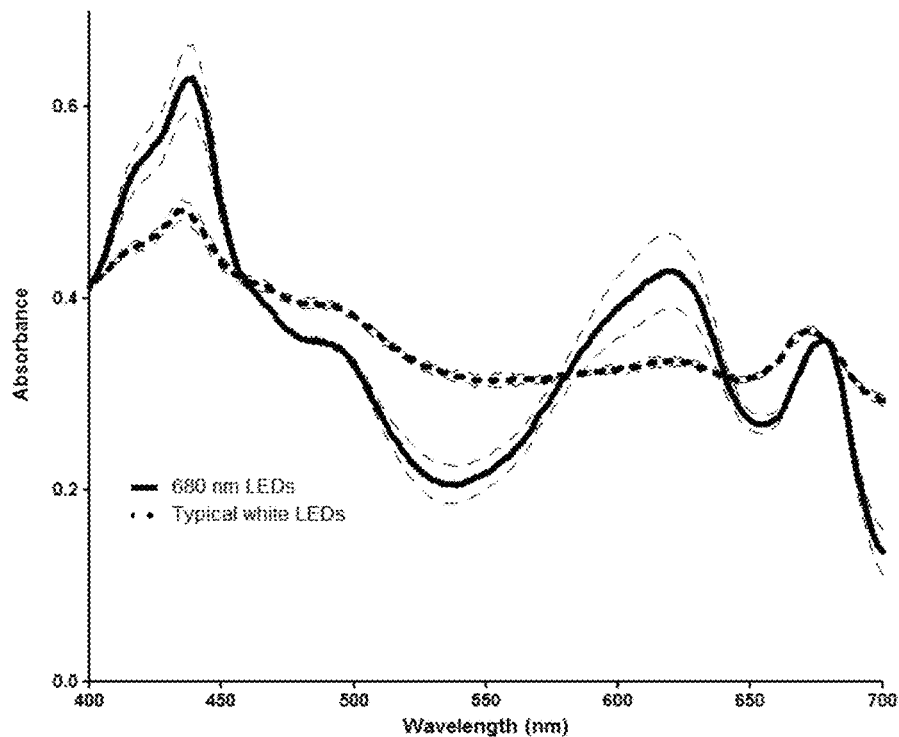
FIG. 5. Absorbance spectra of Phycocyanin extracts from *A. platensis*, normalized at 678 nm, cultured under 680 nm LEDs compared to typical while LEDs. Light dashed lines represent error (s.e.m., standard error of the mean). A larger absorption peak representing Phycocyanin can be seen at around 620 nm in the extract from *A. platensis* cultured under 680 nm LEDs.
Figure 6:
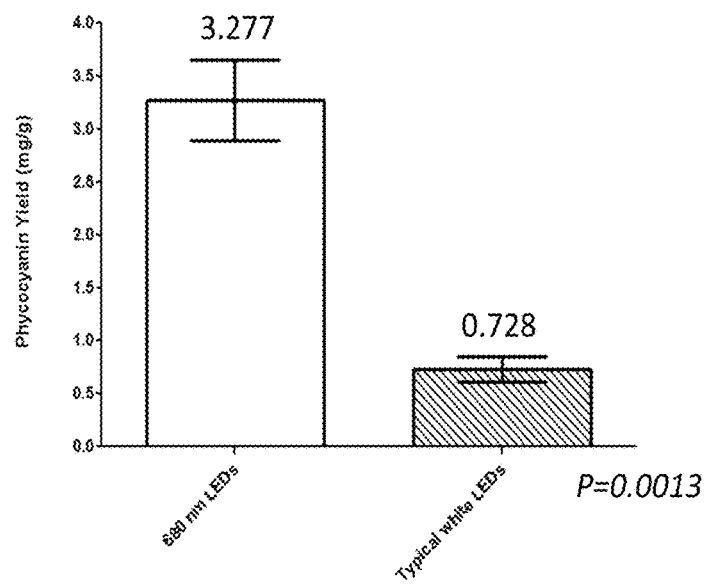
FIG. 6. Average Phycocyanin yield (mg/g) from *A. platensis* cultured under 680 nm LEDs compared to typical white LEDs. Error bars represent standard error of the mean. A large significant increase in Phycocyanin levels can be seen in *A. platensis* through culturing under 680 nm LEDs.

Phycocyanin absorbs at 620 nm. The presence of PC in the extracts of red 680 nm LED batches compared to white LED was much higher (FIGS. 5 & 6). An interesting blue-shift was observed in the second Chlorophyll a peak around 670-680 nm where the peak red 680 nm extract absorption is 677-678 nm and the peak white extract absorption is 673-674 (FIG. 6).

Figure 7:
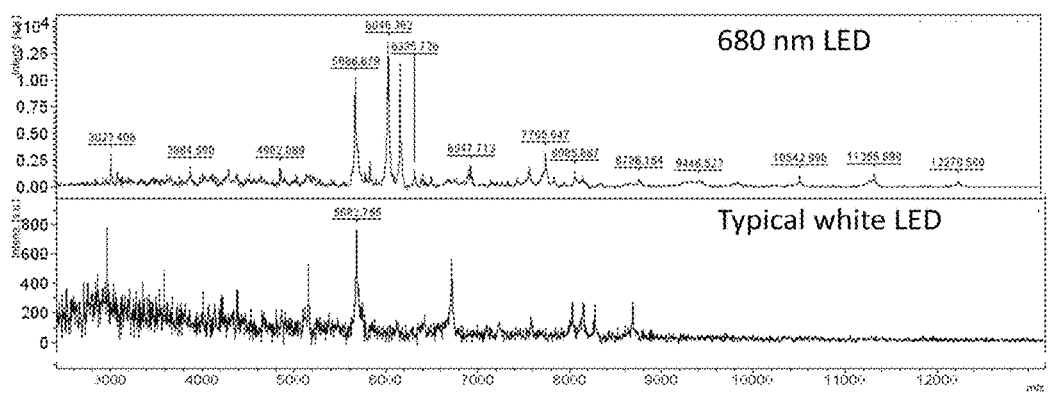
FIG. 7. Mass spectra for *A. platensis* cultures cultured under 680 nm LEDs compared to typical white LEDs show differences in abundant proteins under the two light conditions.

PC concentration was increased 5-fold on average (at least nine samples) through culturing under red 680 nm compared to white LED light and there was a slightly higher PC purity under red 680 nm LED light compared to white (FIG. 7 table). Visual colour differences were observed in the culture most likely resulting from increased PC content of the cells cultured under red 680 nm light (FIG. 7). In another experiment, we found that the PC concentration increased more than 10-fold (data not shown).

Example X: Results: MS Analysis

Figure 8:
FIG. 8. Left shows *A. platensis* culture (top) and extract (bottom) from culturing under typical white LED. Right shows *A. platensis* culture (top) and extract (bottom) from culturing under 680 nm LED.

Whole cell MALDI spectra showed differences in abundant proteins from culturing under red 680 nm compared to white LED light (FIG. 8).

Example XI: Results: Leaching Differences

Figure 9:
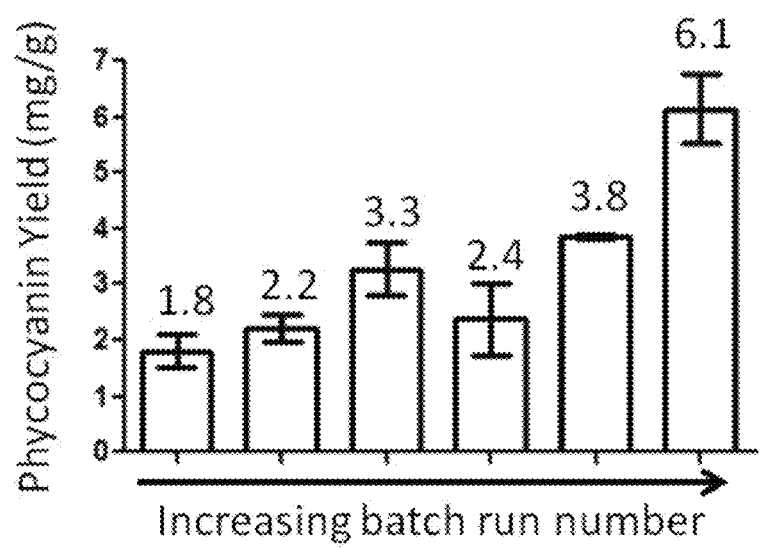
FIG. 9. Average Phycocyanin yield (mg/g) for separate batches of *A. platensis*, inoculated from the previous batch, cultured under 680 nm LEDs shows an increasing yield of Phycocyanin with each subsequent run, likely indicating *A. platensis* is undergoing continual adaptation to enable utilization of 680 nm light more efficiently in photosynthesis.
Figure 10:
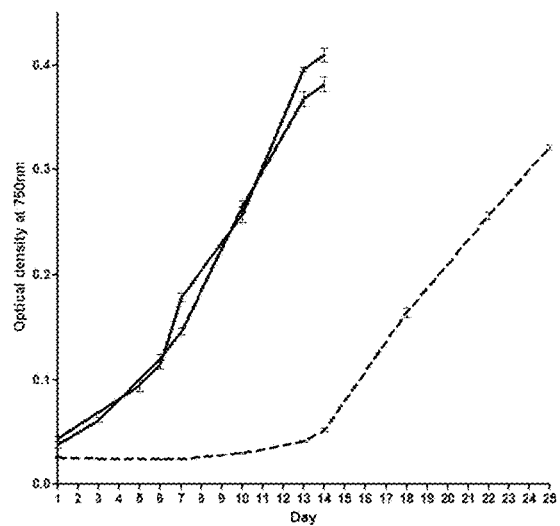
FIG. 10. Growth curves for *A. platensis* batch cultures under 680 nm light. Dashed line shows *A. platensis* culture undergoing acclimatization for utilization of 680 nm light. A lag phase where acclimatization is occuring, is present up to day 14.
Figure 11:
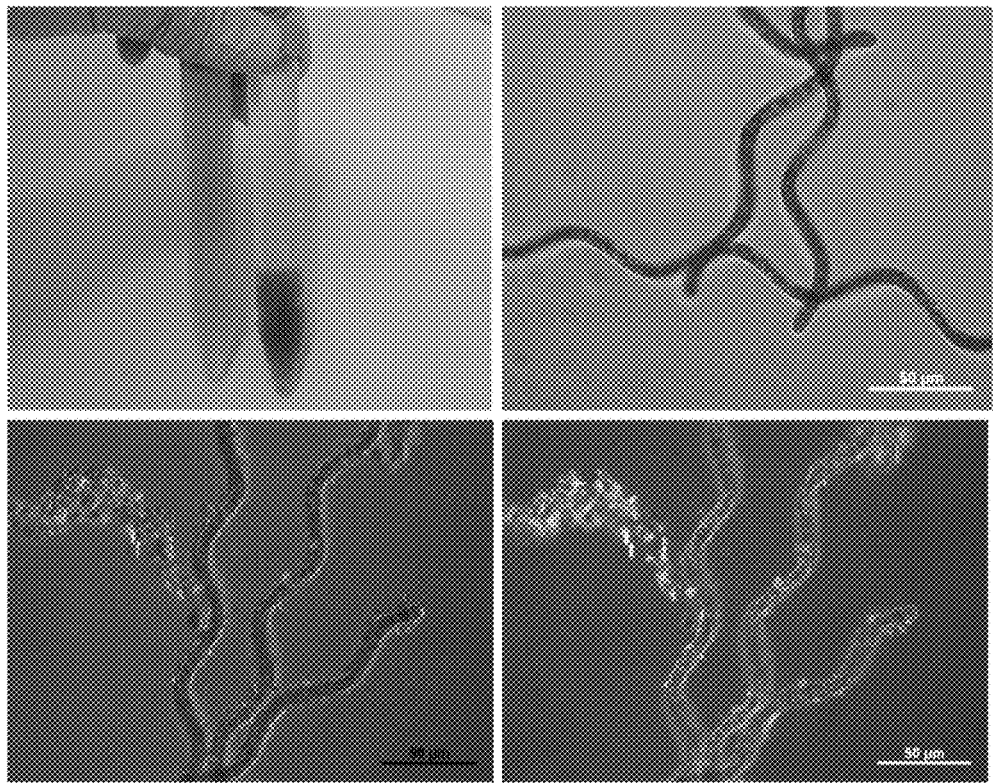
FIG. 11. Top left: Flocculation of higher Phycocyanin-yielding *A. platensis* cultured under 680 nm LEDs. Microscope images show presence of crystals on *A. platensis* trichomes in flocculated cultures (bottom), absent in non-flocculating culture, indicating increase in extracellular polysaccharide, possibly as a stress response.

When discarding the samples prepared for MS analysis, a high concentration of PC had leached into solution in the red 680 nm samples (FIG. 9). By eye the colour difference in leached PC was substantially higher in the red 680 nm culture compared to white LED light, looking much greater than a 5-fold increase. This indicated a possible difference in the PC leaching characteristics in the red 680 nm culture, which may be beneficial to downstream processing (DSP). Culturing under 680 nm light may increase the leaching of PC from the biomass. This is clearly an unexpectedly superior result that could not have been predicted by one of skill in the art.

Example XII: Results: Culture Aggregation

Culturing under 680 nm light may also increase aggregation of the culture, with benefits to DSP. Aggregation may be a result of increased production of extracellular polysaccharide (EPS) as a stress response. This is clearly an unexpectedly superior result that could not have been predicted by one skilled in the art. Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

REFERENCES

[1] Vonshak, A. 1997. *Spirulina Platensis Arthrospira: Physiology, Cell-Biology And Biotechnology*. CRC Press, London.

[2] Gonzalez, R. et al. 1999. Anti-inflammatory activity of phycocyanin extract in acetic acid-induced colitis in rats. *Pharmacological Research* 39(1): 55-59.

[3] Romay, C. et al. 1998. Antioxidant and anti-inflammatory properties of C-phycocyanin from blue-green algae. *Inflammation Research* 47: 36-41.

[4] Pinero Estrada, J. E., Bermejo Bescos, P., and Villar del Fresno, A. M. 2001. Antioxidant activity of different fractions of *Spirulina platensis* protean extract. *Il Farmaco* 56: 497-500.

[5] Belay, A. 2002. The Potential Application of *Spirulina* (*Arthrospira*) as a Nutritional and Therapeutic Supplement in Health Management. *The Journal of the American Nutraceutical Association* 5(2): 27-48.

[6] Kirk, J. O. T. 2000. *Light & Photosynthesis in Aquatic Systems*. Second ed. Cambridge University Press, Cambridge.

[7] Wang, R. T., Stevens, C. L. R., and Myers, J. 1977. Action spectra for photoreactions i and ii of photosynthesis in the blue-green alga anacystis nidulans. *Photochemistry and Photobiology* 25(1): 103-108.

[8] Johnson, J. D. 2006. *The Manganese-calcium oxide cluster of Photosystem II and its assimilation by the Cyanobacteria*. (Last accessed 20 Jul. 2012). Available at: www.chm.bris.ac.uk/motm/oec/motmc.htm.

[9] Habib, M. A. B., Parvin, M., Huntington, T. C., and Hasan, M. R. 2008. *A review on culture, production and use of spirulina as food for humans and feeds for domestic animals and fish*. FAO Fisheries and Aquaculture: Rome.

[10] Bennett, A., Bogorad, L. 1973. Complementary chromatic adaptation in a filamentous blue-green alga. *The Journal of Cell Biology* 58(2): 419-435.

[11] Bogorad, L. 1975. Phycobiliproteins and complementary chromatic adaptation. *Annual Review of Plant Physiology* 26: 369-401.

[12] Walter, A. et al. 2011. Study of phycocyanin production from *Spirulina platensis* under different light spectra. *Brazilian Archives of Biology and Technology* 54: 675-682.

[13] Wang, C.-Y., Fu, C.-C., and Liu, Y.-C. 2007. Effects of using light-emitting diodes on the cultivation of *Spirulina platensis*. *Biochemical Engineering Journal* 37(1): 21-25.

[14] Griffiths, M. J., Garcin, C., van Hille, R. P., and Harrison, S. T. L. 2011. Interference by pigment in the estimation of microalgal biomass concentration by optical density. *Journal of Microbiological Methods* 85(2): 119-123.

[15] Zhang, Y.-M. and Chen, F. 1999. A simple method for efficient separation and purification of c-phycocyanin and allophycocyanin from *Spirulina platensis*. *Biotechnology Techniques* 13(9): 601-603.

[16] Boussiba, S. and Richmond, A. E. 1979. Isolation and characterization of phycocyanins from the blue-green alga *Spirulina platensis*. *Archives of Microbiology* 120(2): 155-159.

[17] Sudhir et al. 2005. The Effects of Salt Stress on Photosynthetic Electron Transport and Thylakoid Membrane Proteins in the Cyanobacteium *Spirulina platensis*. *Journal of Biochemistry and Molecular Biology* 38: 481-485.

[18] Verma, K., Mohanty, P. 2000. Changes of the photosynthetic apparatus in *Spirulina* cyanobacterium by sodium stress. *Z Naturforsch C* 55: 16-22.

[19] Farges, B., Laroche, C., Cornet, J. F., and Dussap, C. G. 2009. Spectral kinetic modeling and long-term behavior assessment of *Arthrospira platensis* growth in photobioreactor under red (620 nm) light illumination. *Biotechnol Prog* 25(1): 151-62.

We claim:

1. A system for producing increased levels of phycocyanin, the system comprising a vessel and a lamp, wherein the lamp provides a source of light, wherein the light consists of electromagnetic radiation consisting of a wavelength of between 670 and 690 nm, and wherein the vessel further comprises a cyanobacteria in a growth medium, and wherein the cyanobacteria synthesizes increased levels of phycocyanin compared to that of cyanobacteria separately cultured in the presence of white light.

2. The system of claim 1, wherein the cyanobacteria is *Arthrospira* or *Spirulina*.

3. The system of claim 1, wherein the electromagnetic radiation comprises a maximum wavelength emission of 680 nm.

4. The system of claim 1, wherein the increased levels of phycocyanin are at least 4.5-fold greater than levels of synthesized phycocyanin in the same cyanobacteria separately cultured in the presence of white light.

5. The system of claim 1, wherein the vessel is selected from the group consisting of a tank, a bioreactor, a pond, and an open raceway.

* * * * *